United States Patent
Servidio (10) Patent No.: US 7,871,442 B2
(45) Date of Patent: Jan. 18, 2011

(54) KNEE PROSTHESIS WITH FOUR DEGREES FREEDOM

(75) Inventor: Damon Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 317 days.

(21) Appl. No.: 11/998,842

(22) Filed: Nov. 30, 2007

(65) Prior Publication Data

US 2009/0143866 A1 Jun. 4, 2009

(51) Int. Cl.
A61F 2/38 (2006.01)
(52) U.S. Cl. .................................. 623/20.27
(58) Field of Classification Search ... 623/20.24–20.31, 623/20.14, 20.15, 20.12, 20.11, 20.13
See application file for complete search history.

(56) References Cited

U.S. PATENT DOCUMENTS

| | | | | |
|---|---|---|---|---|
| 3,696,446 A * | 10/1972 | Bousquet et al. | ......... | 623/20.26 |
| 3,765,033 A * | 10/1973 | Goldberg et al. | ......... | 623/20.26 |
| 3,837,009 A * | 9/1974 | Walker | .......... | 623/20.26 |
| 3,869,729 A * | 3/1975 | Attenborough | .......... | 623/20.25 |
| 3,934,272 A * | 1/1976 | Wearne et al. | ........... | 623/20.26 |
| 3,996,624 A | 12/1976 | Noiles | | |
| 4,064,568 A * | 12/1977 | Grundei et al. | .......... | 623/20.26 |
| 4,136,405 A * | 1/1979 | Pastrick et al. | ........... | 623/20.25 |
| 4,219,893 A | 9/1980 | Noiles | | |
| 4,262,368 A * | 4/1981 | Lacey | ....................... | 623/20.25 |
| 4,301,553 A * | 11/1981 | Noiles | ..................... | 623/20.25 |
| 4,462,120 A | 7/1984 | Rambert et al. | | |
| 5,139,521 A * | 8/1992 | Schelhas | ................... | 623/20.25 |
| 5,314,481 A * | 5/1994 | Bianco | ..................... | 623/20.25 |
| 5,358,527 A | 10/1994 | Forte | | |
| 5,370,701 A * | 12/1994 | Finn | ........................ | 623/20.25 |
| 5,411,555 A | 5/1995 | Nieder et al. | | |
| 5,458,644 A * | 10/1995 | Grundei | .................... | 623/20.24 |
| 5,702,466 A * | 12/1997 | Pappas et al. | ............ | 623/20.29 |
| 5,755,804 A * | 5/1998 | Schmotzer et al. | ........ | 623/20.24 |
| 5,800,552 A * | 9/1998 | Forte | ........................ | 623/20.27 |
| 5,824,096 A * | 10/1998 | Pappas et al. | ............. | 623/23.39 |
| 5,954,770 A * | 9/1999 | Schmotzer et al. | ........ | 623/20.24 |
| 6,019,794 A | 2/2000 | Walker | | |
| 6,099,570 A * | 8/2000 | Livet et al. | ................ | 623/20.21 |
| 6,139,580 A * | 10/2000 | Wurzinger et al. | ........ | 623/20.26 |
| 6,264,696 B1 * | 7/2001 | Reigner et al. | ............ | 623/20.24 |
| 6,296,666 B1 * | 10/2001 | Gardner | .................... | 623/20.29 |
| 6,485,519 B2 * | 11/2002 | Meyers et al. | ............. | 623/20.24 |
| 6,488,711 B1 * | 12/2002 | Grafinger | .................. | 623/20.24 |
| 6,491,726 B2 * | 12/2002 | Pappas | ..................... | 623/20.29 |
| 6,755,864 B1 * | 6/2004 | Brack et al. | ............... | 623/20.29 |
| 6,770,098 B1 * | 8/2004 | Hauri et al. | ............... | 623/20.26 |
| 6,984,249 B2 * | 1/2006 | Keller | ....................... | 623/20.24 |
| 6,986,791 B1 * | 1/2006 | Metzger | ................... | 623/20.24 |
| 7,232,465 B2 * | 6/2007 | Keller | ....................... | 623/20.24 |
| 7,572,292 B2 * | 8/2009 | Crabtree et al. | ........... | 623/20.24 |
| 7,591,855 B2 * | 9/2009 | Keller | ....................... | 623/20.24 |

(Continued)

*Primary Examiner*—Alvin J. Stewart
(74) *Attorney, Agent, or Firm*—Lerner, David, Littenberg, Krumholz & Mentlik, LLP (57) ABSTRACT

Knee prosthesis for implanting in a knee joint has a femoral component, a tibial component and a hinge connecting the femoral component and the tibial component. The femoral component rotates around the transverse axis passing through center of the hinge and the center of rotation of the femoral component moves substantially along proximal-distal axis upon flexion of the knee joint.

8 Claims, 5 Drawing Sheets

U.S. PATENT DOCUMENTS

| | | | |
|---|---|---|---|
| 7,658,767 B2 * | 2/2010 | Wyss | 623/20.29 |
| 2004/0143339 A1 | 7/2004 | Axelson et al. | |
| 2004/0225368 A1 * | 11/2004 | Plumet et al. | 623/20.15 |
| 2004/0249467 A1 * | 12/2004 | Meyers et al. | 623/20.24 |
| 2005/0107886 A1 | 5/2005 | Crabtree et al. | |
| 2005/0246028 A1 * | 11/2005 | Pappas et al. | 623/20.25 |
| 2008/0004708 A1 * | 1/2008 | Wyss | 623/20.24 |
| 2008/0167722 A1 * | 7/2008 | Metzger et al. | 623/20.36 |
| 2009/0024221 A1 * | 1/2009 | Ball | 623/20.11 |
| 2009/0088860 A1 * | 4/2009 | Romeis et al. | 623/20.24 |
| 2009/0125116 A1 * | 5/2009 | Crabtree et al. | 623/20.24 |
| 2009/0149964 A1 * | 6/2009 | May et al. | 623/20.15 |

* cited by examiner (PRIOR ART)

KNEE PROSTHESIS WITH FOUR DEGREES FREEDOM

BACKGROUND OF THE INVENTION

1. Field of the Invention

The present invention relates generally to knee prosthesis and, more specifically, to hinged knee prosthesis that achieves better emulation of natural knee joint kinematics in a prosthetic knee.

2. Brief Description of the Prior Art

During articulation of a natural knee joint, flexion between the tibia and the femur takes place about a transverse axis while, at the same time, some relative rotation between the tibia and the femur occurs about a longitudinal axis. Such flexion and rotation is necessary to carry out a normal gate cycle. It has been established that in full extension the tibia is rotationally displaced, relative to the femur, by approximately 2-3 degree. As the natural knee flexes, the tibia rotates internally. According to previous studies, about 5 degree of rotation ordinarily occurs as the knee is articulated from 0 degree to 10 degree of flexion; thereafter, little further rotation occurs up to at least about 45 degree of flexion. Total rotation at 110 degree of flexion is approximately 20 degree.

Rotational stability of the natural knee is provided by the collateral and cruciate ligaments. The cruciate ligaments deter uncontrolled internal rotation within a certain range of flexion of the knee, while the collateral ligaments provide transverse stability and deter uncontrolled external rotation of the tibia. Where the natural knee is replaced by a total knee prosthesis, either the anterior cruciate ligament or both the anterior and posterior cruciate ligaments ordinarily are sacrificed. In the instances where the knee prosthesis is constrained to supply the stability ordinarily provided by the sacrificed ligaments it is desirable for the knee prosthesis to mimic the natural knee as closely as possible.

Early hinged knee designs had a fixed hinge connecting the tibial and femoral components. This hinge had a fixed center of rotation, and as a result any "natural" rotations and translations that may have occurred between the femur and tibia during flexion of the knee manifested themselves as forces at the bone-implant interface. Due to these forces, early hinged knee designs tended to fail by becoming loose at the bone-implant interface.

Subsequently improvements in hinged knee designs have resulted in the hinge being associated with a circular post that is inserted into the tibial component. The effect of this post is that the hinge no longer has a fixed center of rotation. A hinge on a circular post is able to both translate along one axis and rotate about that axis. This design results in lower forces being transmitted to the bone-implant interface during knee flexion, as a result increasing the longevity of hinged total knee replacements. However, any anterior-posterior translation of the center of rotation is prevented. Since the movement of the femoral component of these hinged knee designs has a translational component in anterior-posterior direction with respect to the tibial component, forces are generated that act to weaken the bone-implant interface. The generation of these forces is avoided in non-hinged total knee replacement prosthesis because the femoral component and the tibial component are not rigidly connected via a hinge.

Non-hinged total knee replacements rely on the knee ligaments and other soft tissues to provide stability to the knee joint and in part dictate the relative motion between the femoral and tibial components. As a result of the soft tissue guiding the relative motion of the knee between the femoral and tibial components, the knee moves in a more "natural" manner than can be provided by existing hinged knee designs. Extra amount of stability can be provided by a post on the tibial component interfacing with a cam on the femoral component during knee flexion. Unlike a hinge, the post and cam are not connected to each other in a fixed manner and therefore allow translational and rotational degrees of freedom. Such knee replacement prostheses are conventionally known as posterior stabilized knee replacement prosthesis. One example of a posterior stabilized knee replacement prosthesis is Stryker's Scorpio family of knee replacement prosthesis. U.S. Pat. No. 7,160,330 describes a posterior stabilized knee replacement prosthesis that has a articular surface at least a portion of which has constant radius. U.S. Pat. No. 7,160,330 is incorporated herein by reference in its entirety. Since these posterior stabilized systems mimic natural knee kinematics, they do not create excessive forces at the bone-implant interface. However, posterior stabilized knee replacement prosthesis can get dislocated. Therefore, often, if additional stability is required over that afforded by a design with a post-cam articulation, a hinged knee may be required.

Thus, there exists a need for a total knee replacement design that offers the benefits of both a hinged knee (stability despite lack of soft tissue constraint) and a non-hinged knee (natural knee kinematics).

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

SUMMARY OF THE INVENTION

A Knee prosthesis includes a femoral component and a tibial component. A box-like structure is formed in the proximally facing surface of femoral component on the opposite side of condylar surfaces. The box-like structure has a horizontal wall and two opposing vertical walls. Circular openings are formed in the vertical walls. At least one bushing is inserted in the circular openings. A pin may be inserted in the bushings.

The tibial component has a hinge shaft that slides in a proximal-distal direction and rotates about the axis of the hole in the tibial component. The hinge shaft has an end that may be inserted in the hole and an end having an opening. The opening is sized to allow the pin to slide in the opening. The end of the hinge shaft having the opening is narrower than the distance between the vertebral walls of the box-like structure.

In use, the femoral component is mounted on the femur and the tibial component is mounted on tibia using techniques known to one skilled in the art. When the knee prosthesis is implanted in the body, the femoral component and the tibial component are hingedly connected to each other. In the implanted state, the pin is passing through the opening in the tibial component hinge shaft which is located within the box structure. The pin, in turn, is also supported in bushings. The pin forms the hinge pin of the joint when the femoral component is assembled with the tibial component. In the implanted state, the femoral component can rotate with respect to the tibial component by virtue of the pin being able to rotate in the hinge shaft opening. Since the pin is slidably mounted in the opening, the femoral component can also slide with respect to the tibial component in medial-lateral direction. Additionally, the hinge shaft is slidably inserted in the hole of tibial component. The hinge shaft is not constrained from rotating in hole. This allows the femoral component to rotate around the longitudinal axis of the hinge shaft. The hinge shaft also moves in up-down direction in the hole in the tibial component thereby allowing the center of rotation of the femoral component to vary in vertical direction. The four degrees of freedom described above allow knee prosthesis to mimic the articulation between tibia and femur in a natural knee joint.

The femoral component is constructed such that the center of rotation of the femoral component moves substantially along a proximal-distal axis of the tibia when the joint is flexed. By designing the femoral component in a manner that the center of rotation of the femoral component mimics a point on the femoral component of the posterior stabilized knee prosthesis that moves along a proximal-distal axis, the hinged knee prosthesis can be made to exhibit knee kinematics similar to that of posterior stabilized knee prosthesis.

An object of the present invention is to design a femoral component in a manner that the center of rotation of the femoral component mimics a point on the femoral component of a posterior stabilized knee prosthesis that moves along a proximal-distal axis. Thereby, the hinged knee prosthesis of the present invention can be made to exhibit knee kinematics similar to that of a posterior stabilized knee prosthesis.

Another object of the present invention is to provide knee prosthesis for implanting in a knee joint. The prosthesis includes a femoral component and a tibial component having a proximal-distal axis. A hinge connects the femoral component and the tibial component. The femoral component rotates around a transverse axis passing through center of the hinge. The center of rotation of the femoral component moves substantially along the proximal-distal axis upon flexion of the knee joint.

DETAILED DESCRIPTION

Figure 1:
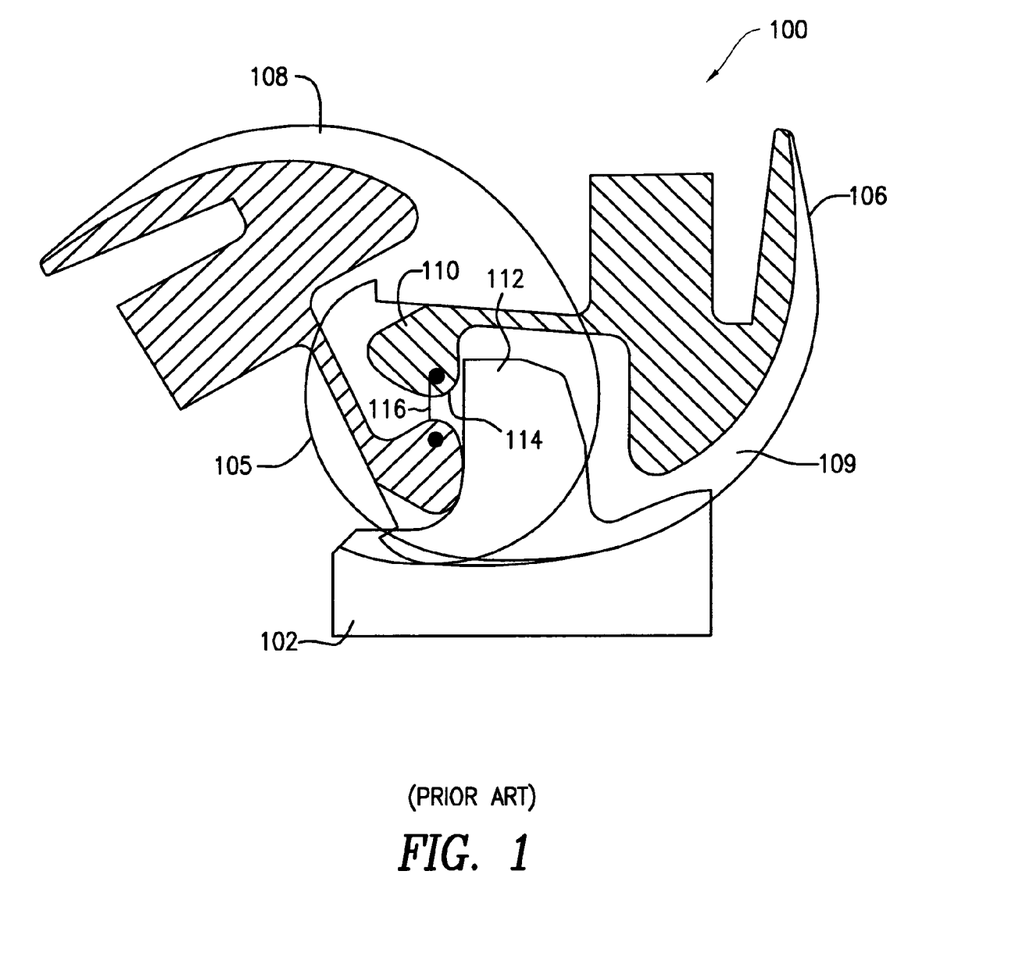
FIG. 1 is a cross sectional view of a posterior stabilized knee prosthesis showing the femoral component in relation to the tibial component at zero degree and one hundred and twenty degree flexion.

FIG. 1 shows a known constant radius posterior stabilized knee prosthesis 100. The knee prosthesis 100 includes a tibial component 102 and a femoral component 104. The femoral component 104 is shown in two positions 106 and 108. First position 106 shows the placement of femoral component 104 when the joint is in zero degree flexion (i.e., extension). Second position 108 shows the placement of femoral component 104 when the joint is in one hundred and twenty degree flexion. The condoyles 105 of femoral component 104 have a second constant radius approximately between 0-120 degrees. The femoral component 104 has a cam 110. Cam 110 has a first constant radius 114. The tibial component 102 has a post 112. Cam 110 mates with post 112. As the leg flexes from 0-120 degrees the center of curvature of the first constant radius 114 travels substantially along a line 116 that is parallel to the proximal-distal axis of the tibial component. Thus, if a hinge connecting the femoral component and tibial component has its center located at a point corresponding to the center of curvature of the first constant radius 114, such knee prosthesis would mimic the natural knee kinematics of a post-cam design.

Figure 2:
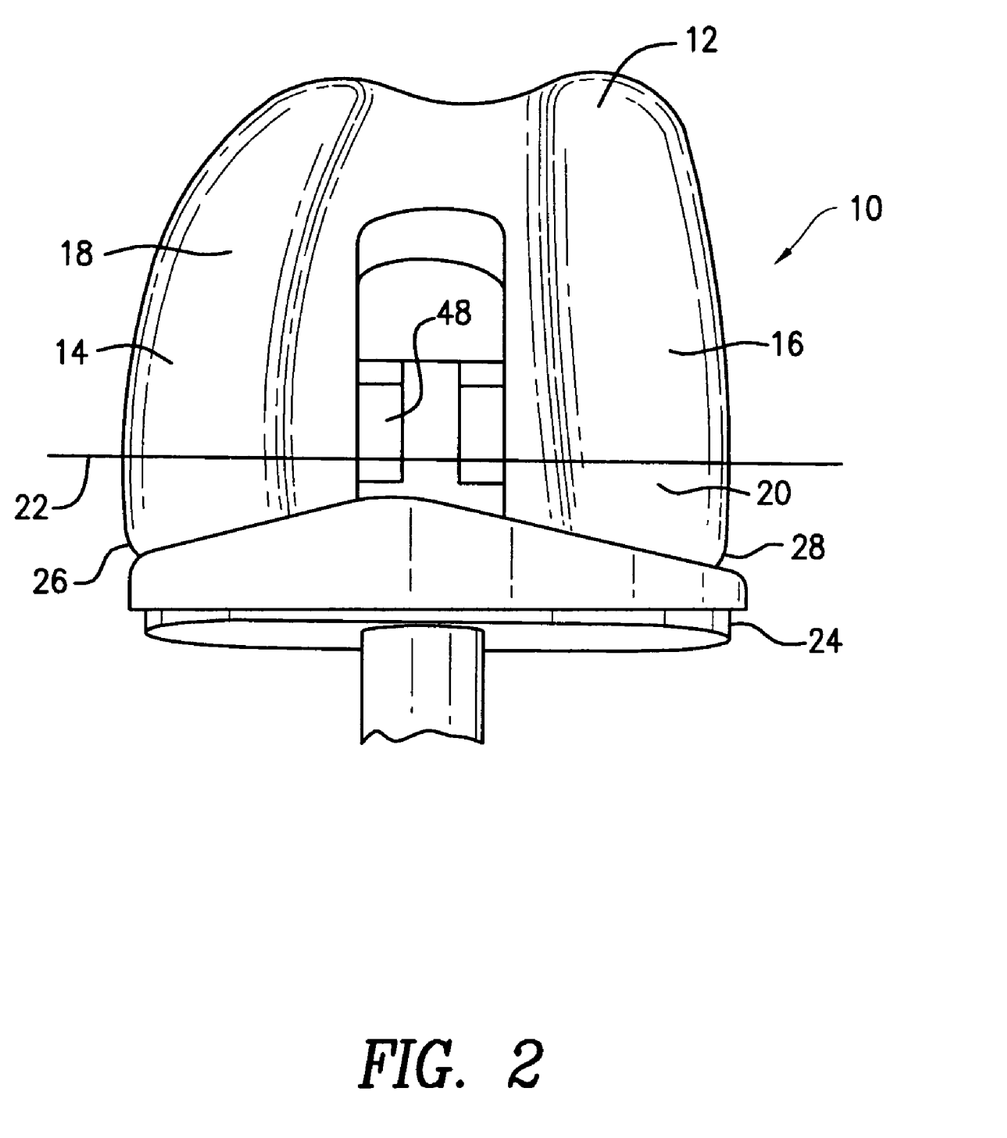
FIG. 2 is an isometric view of an embodiment of knee prosthesis of present invention.

FIG. 2 shows a knee prosthesis 10 constructed in accordance with the present invention. Knee prosthesis 10 includes a femoral component 12 having a lateral condyle 14 and a medial condyle 16. Each condyle 14 and 16 includes a condylar surface 18 and 20, respectively, and the condylar surfaces 18 and 20 have a common axis of rotation 22 extending transversely across the femoral component 12. In the preferred embodiment, axis of rotation 22 is located on the femoral component 12 such that upon implanting of the knee prosthesis 10, axis of rotation 22 will be parallel with a line extending transversely between the medial and lateral ligament attachment points on the femur of the natural knee. A tibial component 24 has a lateral articular surface 26 for engagement with lateral condylar surface 18 of lateral condyle 14, and a medial articular surface 28 for engagement with medial condylar surface 20 of medial condyle 16.

Figure 3:
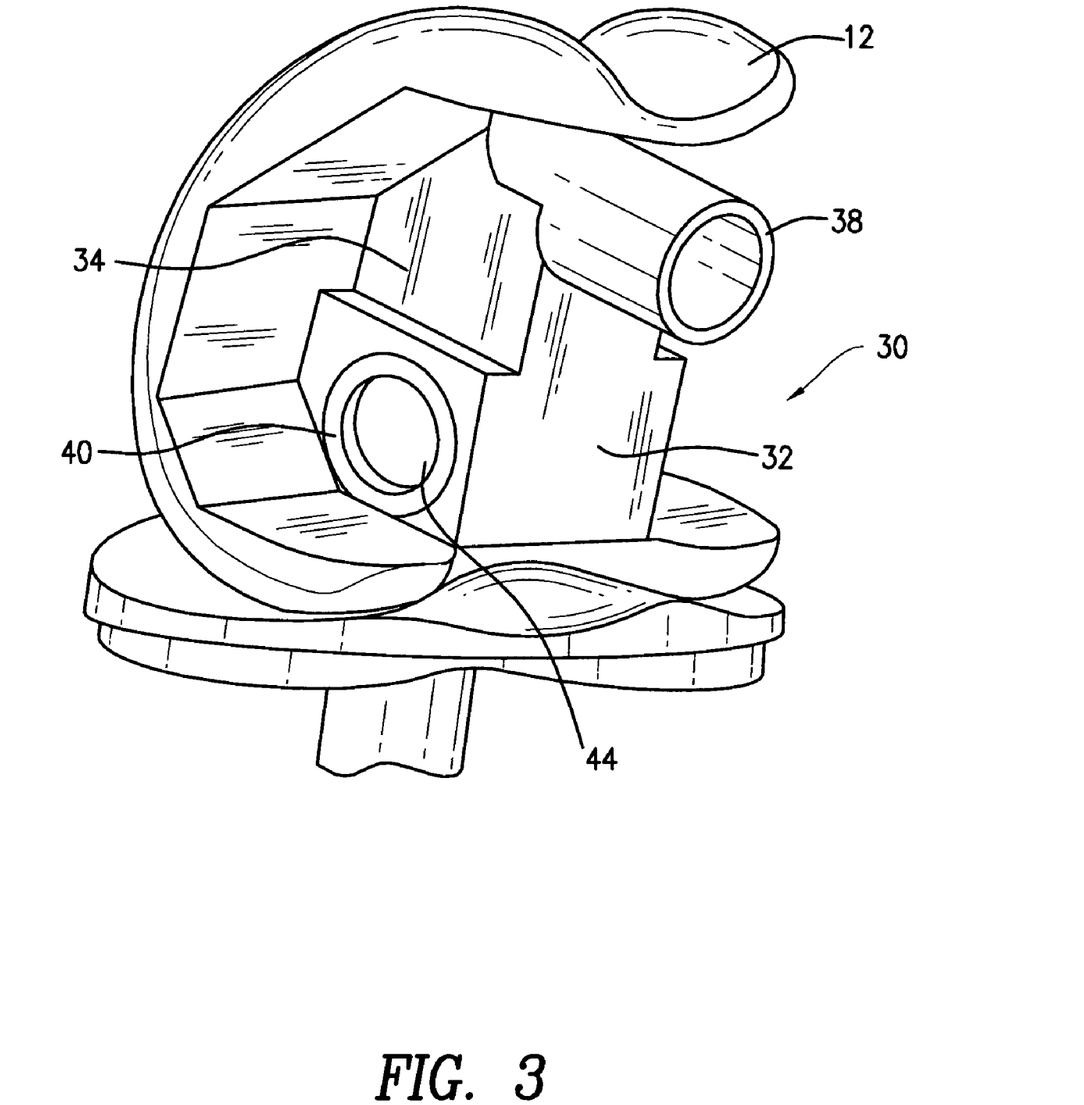
FIG. 3 is an isometric view of the knee prosthesis of FIG. 2 showing box like structure.
Figure 4:
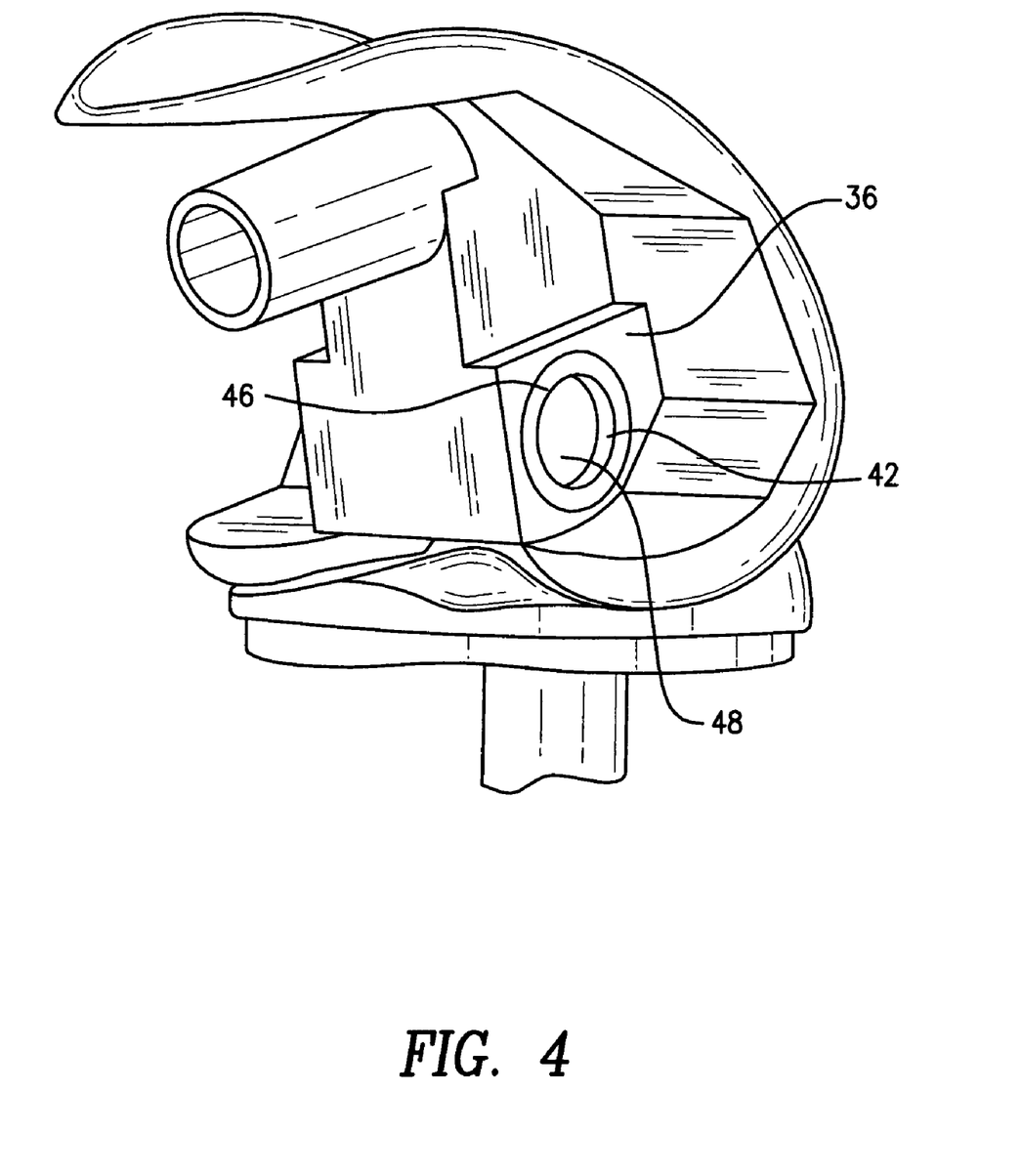
FIG. 4 is another isometric view of the knee prosthesis of present invention.

FIG. 3 shows a box like structure 30 formed in the back of femoral component 12 on the opposite side of the condylar surfaces 18 and 20. Box like structure 30 has a horizontal wall 32 and two opposing vertical walls 34 and 36 (FIG. 4). A stem portion 38 projects from wall 32. Stem portion 38 can accommodate a stem that is inserted in femur to attach femoral component 12 to the femur. A circular opening 40 is formed in wall 34. A similar circular opening 42 (FIG. 4) is formed in wall 36. A bushing 44 is inserted in circular opening 40 and a bushing 46 is inserted in circular opening 42. A pin 48 (see FIG. 2) may be inserted in bushings 44 and 46.

Figure 5:
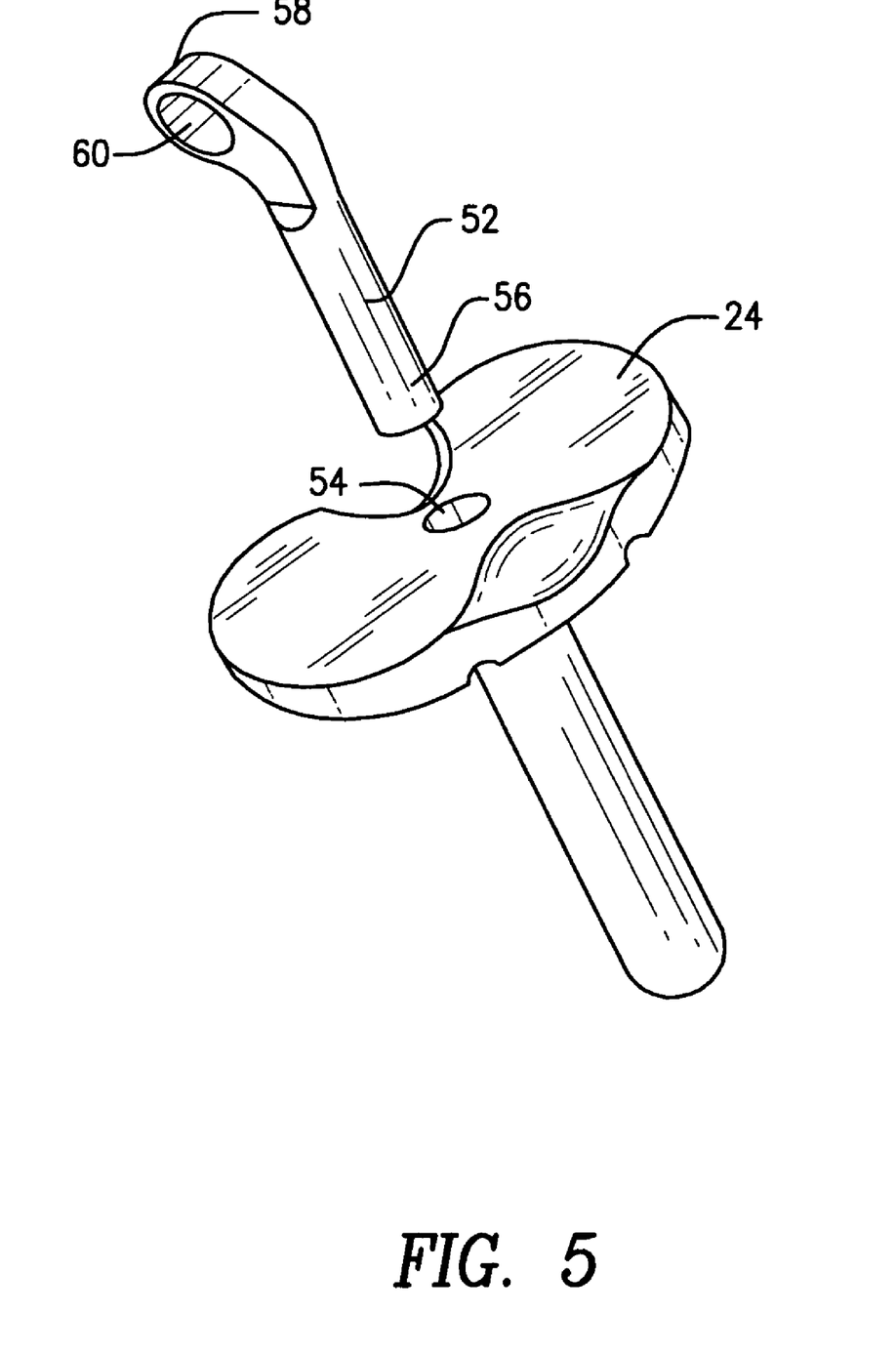
FIG. 5 is an isometric view of the tibial component and hinge shaft of the knee prosthesis of FIG. 1.

FIG. 5 shows the tibial component 24 and a hinge shaft 52 that slides in a proximal-distal direction and rotates in a hole 54 in the tibial component 24. Shaft 52 has an end 56 that may be inserted in the hole 54 and an end 58 having an opening 60. Opening 60 is sized to allow pin 48 to slide and rotate in the opening 60.

In use, femoral component 12 is mounted on the femur and tibial component 24 is mounted on tibia using techniques known to one skilled in the art. The femur and tibia may be prepared for mounting of the femoral component 12 and the tibial component 24 using one of many techniques known to one skilled in the art. The box cuts made on the femur to mount femoral component 12 may be same as the box cuts that are required to mount a femoral component of a non-hinged knee prosthesis having a post and a box. When knee prosthesis 10 is implanted in the body, femoral component 12 and tibial component 24 are hingedly connected to each other. In the implanted state, pin 48 is passing through opening 60 in shaft 52. Pin 48, in turn, is also supported in bushings 44 and 46. The pin 48 forms the hinge pin of the joint when the femoral component 12 is assembled with tibial component 24. The femoral component rotates around the longitudinal axis passing through center of the hinge pin 48. The femoral component 12 is constructed such that the center of rotation of the femoral component 12 moves substantially along a proximal-distal axis of the tibia when the joint is flexed. The center of rotation of the femoral component 12 is located in a place that corresponds to the center of curvature of the first constant radius 114 of the posterior stabilized knee prosthesis 100. Therefore, by designing the femoral component 12 in a manner that the center of rotation of the femoral component 12 mimics a point on the femoral component 104 (of the posterior stabilized knee prosthesis 100) that moves along a proximal-distal axis, the hinged knee prosthesis 30 can be made to exhibit knee kinematics similar to that of posterior stabilized knee prosthesis 100. In the implanted state, femoral component 12 can rotate with respect to tibial component 24 by virtue of pin 48 being able to rotate in opening 60. Since pin 48 is slidably mounted in opening 60, femoral component can also slide with respect to tibial component 24 in medial-lateral direction. Additionally, shaft 52 is slidably inserted in hole 54 of tibial component 24. Shaft 52 is not constrained from rotating in hole 54. This allows femoral component 12 to rotate around a longitudinal axis that is parallel to the longitudinal axis of shaft 52. Shaft 52 also moves in up-down direction in hole 54 thereby allowing the center of rotation of femoral component 12 to vary in vertical direction. The four degrees of freedom described above allow knee prosthesis 10 to mimic the articulation between tibia and femur in a natural knee joint.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

In use, femoral component 12 is mounted on the femur and tibial component 24 is mounted on tibia using techniques known to one skilled in the art. The femur and tibia may be prepared for mounting of the femoral component 12 and the tibial component 24 using one of many techniques known to one skilled in the art. The box cuts made on the femur to mount femoral component 12 may be same as the box cuts that are required to mount a femoral component of a non-hinged knee prosthesis having a post and a box. When knee prosthesis 10 is implanted in the body, femoral component 12 and tibial component 24 are hingedly connected to each other. In the implanted state, pin 48 is passing through opening 60 in shaft 52. Pin 48, in turn, is also supported in bushings 44 and 46. The pin 48 forms the hinge pin of the joint when the femoral component 12 is assembled with tibial component 24. The femoral component rotates around the longitudinal axis passing through center of the hinge pin 48. The femoral component 12 is constructed such that the center of rotation of the femoral component 12 moves substantially along a proximal-distal axis of the tibia when the joint is flexed. In other words, the femoral component rotates about the hinge axis, and the hinge axis moves substantially along an axis substantially parallel to the proximal-distal axis of the tibial component upon flexion of the knee joint. The center of rotation of the femoral component 12 is located in a place that corresponds to the center of curvature of the first constant radius 114 of the posterior stabilized knee prosthesis 100. Therefore, by designing the femoral component 12 in a manner that the center of rotation of the femoral component 12 mimics a point on the femoral component 104 (of the posterior stabilized knee prosthesis 100) that moves along a proximal-distal axis, the hinged knee prosthesis 30 can be made to exhibit knee kinematics similar to that of posterior stabilized knee prosthesis 100. In the implanted state, femoral component 12 can rotate with respect to tibial component 24 by virtue of pin 48 being able to rotate in opening 60. Since pin 48 is slidably mounted in opening 60, femoral component can also slide with respect to tibial component 24 in medial-lateral direction. Additionally, shaft 52 is slidably inserted in hole 54 of tibial component 24. Shaft 52 is not constrained from rotating in hole 54. This allows femoral component 12 to rotate around a longitudinal axis that is parallel to the longitudinal axis of shaft 52. Shaft 52 also moves in up-down direction in hole 54 thereby allowing the center of rotation of femoral component 12 to vary in vertical direction. The four degrees of freedom described above allow knee prosthesis 10 to mimic the articulation between tibia and femur in a natural knee joint.

I claim:

1. A knee prosthesis for implanting in a knee joint including a femur and a tibia, the tibia having a longitudinal axis, the prosthesis comprising:
   a femoral component defining a fixed axis of rotation;
   a tibial component defining a hole and having a proximal-distal axis substantially parallel to the longitudinal axis of the tibia; and
   a hinge assembly including a hinge rod and a pin connecting the femoral component and the tibial component, the hinge rod having a circular opening adapted to allow the pin to pass therethrough, the hinge rod adapted to slide in the hole of the tibial component, the hinge assembly defining a hinge axis that is transverse to the proximal-distal axis of the tibial component,
   wherein the femoral component rotates about the hinge axis, and the hinge axis moves substantially along an axis substantially parallel to the proximal-distal axis of the tibial component upon flexion of the knee joint.

2. The knee prosthesis of claim 1, further comprising:
   a box having opposing walls formed on the femoral component;
   the opposing walls each defining a circular aperture; and
   at least one bushing adapted to fit in the circular aperture.

3. The knee prosthesis of claim 2, wherein the hinge rod is capable of translating and rotating in the hole while the pin rotates in the circular apertures of the opposing walls.

4. The knee prosthesis of claim 1, wherein, when compared to a known posterior stabilized knee prosthesis of a post-cam design having a femoral component with a constant radius cam, the fixed axis of rotation of the femoral component is located along an axis corresponding to the center of curvature of the constant radius cam.

5. A knee prosthesis for implanting in a knee joint including a femur and a tibia, the tibia having a longitudinal axis, the prosthesis comprising:
   a tibial component defining a hole and having a proximal-distal axis substantially parallel to the longitudinal axis of the tibia;
   a pin;
   a hinge rod adapted to slide in the hole of the tibial component, the hinge rod having a circular opening adapted to allow the pin to pass therethrough; and
   a femoral component being hinged to the tibial component and defining a fixed axis of rotation,
   wherein the femoral component is adapted to rotate with respect to the tibial component about the proximal-distal axis of the tibial component, the femoral component is adapted to rotate with respect to the tibial component about a hinge axis transverse to the proximal-distal axis, the femoral component is adapted to translate with respect to the tibial component in a medial-lateral direction, and the femoral component is adapted to translate along the proximal-distal axis with respect to the tibial component, and
   wherein the fixed axis of rotation of the femoral component is adapted to translate substantially along an axis substantially parallel to the proximal-distal axis of the tibia component.

6. The knee prosthesis of claim 5, further comprising:
   a box having opposing walls formed on the femoral component;
   the opposing walls each defining a circular aperture; and at least one bushing adapted to fit in the circular aperture.

7. The knee prosthesis of claim 6, wherein the hinge rod is capable of translating and rotating in the hole while the pin rotates in the circular apertures of the opposing walls.

8. The knee prosthesis of claim 7, wherein, when compared to a known posterior stabilized knee prosthesis of a post-cam design having a femoral component with a constant radius cam, the fixed axis of rotation of the femoral component is located along an axis corresponding to the center of curvature of the constant radius.

* * * * *

UNITED STATES PATENT AND TRADEMARK OFFICE
CERTIFICATE OF CORRECTION

| | |
|---|---|
| PATENT NO. | : 7,871,442 B2 |
| APPLICATION NO. | : 11/998842 |
| DATED | : January 18, 2011 |
| INVENTOR(S) | : Damon J. Servidio |

It is certified that error appears in the above-identified patent and that said Letters Patent is hereby corrected as shown below:

On the Title page item (54), insert --OF-- before "FREEDOM".
On the Title page item (57) ABSTRACT, line 4, insert --the-- after "through".
Column 1, line 1, insert --OF-- before "FREEDOM".
Column 1, line 16, delete "is" and insert therefor --are--.
Column 1, line 19, "degree" should read --degrees--.
Column 1, line 20, "degree" should read --degrees--.
Column 1, line 21, "occurs" should read --occur--.
Column 1, line 23, "degree" should read --degrees--.
Column 1, line 24, "degree" should read --degrees--.
Column 2, line 12, "a" should read --an--.
Column 2, line 37, "Knee" should read --knee--.
Column 2, line 39, after "of" insert --the--.
Column 2, line 53, after "on" insert --the--.
Column 2, line 57, delete "is passing" and insert therefor --passes--.
Column 3, line 1, after "of" insert --the--.
Column 3, line 2, after "in" insert --the--.
Column 3, line 40, "degree" should read --degrees--.
Column 3, line 42, after "of", second occurrence, insert --the--.
Column 3, line 45, "box like" should read --box-like--.
Column 3, line 46, after "of", second occurrence, insert --the--.
Column 4, line 23, "box like" should read --box-lite--.
Column 4, line 25, "box like" should read --box-lite--.
Column 4, line 28, after "in" insert --the--.
Column 4, line 41, after "on" insert --the--.
Column 4, line 46, after "be" insert --the--.
Column 4, line 51, "is passing" should read --passes--.
Column 4, line 56, after "through" insert --the--.

Signed and Sealed this
Tenth Day of January, 2012

David J. Kappos
*Director of the United States Patent and Trademark Office*

Column 4, line 59, after "flexed." insert --In other words, the femoral component rotates about the hinge axis, and the hinge axis moves substantially along an axis substantially parallel to the proximal distal axis of the tibial component upon flexion of the knee joint.--.

Column 5, line 5, after "component" insert --12--.

Column 5, delete lines 25 through Column 6, line 4.

Column 8, after "radius" insert --cam--.